United States Patent [19]

Brinkmeyer et al.

[11] Patent Number: 5,220,091
[45] Date of Patent: Jun. 15, 1993

[54] ALKANE DEHYDROGENATION

[75] Inventors: Francis M. Brinkmeyer; Kelly B. Savage; Gyanesh P. Khare; Donald H. Kubicek, all of Bartlesville, Okla.

[73] Assignee: Phillips Petroleum Company, Bartlesville, Okla.

[21] Appl. No.: 842,298

[22] Filed: Feb. 26, 1992

[51] Int. Cl.$^5$ .............................. C07C 5/333
[52] U.S. Cl. ........................ 585/660; 585/661
[58] Field of Search ..................... 585/660, 661

[56] References Cited

U.S. PATENT DOCUMENTS

| | | | |
|---|---|---|---|
| 3,668,151 | 6/1972 | Walker | 252/466 |
| 3,692,701 | 9/1972 | Box, Jr. | 252/466 B |
| 3,880,776 | 4/1975 | Box, Jr. et al. | 252/466 PT |
| 3,957,688 | 5/1976 | Farha, Jr. et al. | 252/455 R |
| 4,088,736 | 5/1978 | Courty et al. | 423/230 |
| 4,152,365 | 5/1979 | Drehman | 585/256 |
| 4,370,310 | 1/1983 | Walker | 423/600 |

Primary Examiner—Patrick P. Garvin
Assistant Examiner—E. D. Irzinski
Attorney, Agent, or Firm—K. K. Brandes

[57] ABSTRACT

A process for dehydrogenating $C_2$-$C_8$ alkanes in the presence of steam and a catalyst composition containing zinc aluminate, a tin oxide and platinum, wherein the zinc aluminate support material has been prepared by calcining zinc oxide and a hydrated alumina (so as to alleviate coking during the dehydrogenation process).

13 Claims, 2 Drawing Sheets

ALKANE DEHYDROGENATION

BACKGROUND OF THE INVENTION

This invention relates to a process for dehydrogenating gaseous alkanes in the presence of steam and a catalyst comprising zinc aluminate, tin oxide(s) and platinum.

The dehydrogenation of gaseous alkanes to alkenes in the presence of steam and catalysts comprising zinc aluminate, tin oxide(s) and platinum is known and has been described in numerous patents, such as U.S. Pat. Nos. 4,902,849, 4,152,365 and 3,957,688. Generally, the catalyst preparation comprises the step of calcining alumina and zinc oxide (and preferably also tin dioxide), followed by impregnation of the formed zinc aluminate (preferably admixed with $SnO_2$) with platinum and calcining. The prior art teaches the use of flame-hydrolyzed alumina (i.e., crystalline alpha- or gamma-alumina) in the preparation of zinc aluminate. Even though catalysts prepared by the prior art method are quite effective in alkane dehydrogenation processes, coke deposition on the catalysts remains an operational problem (because it requires frequent catalyst regeneration by heating in a free oxygen containing gas, such as air). The present invention is directed to the use of a catalyst composition which results in reduced coke formation in an alkane dehydrogenation process.

SUMMARY OF THE INVENTION

It is an object of this invention to provide a process for dehydrogenating gaseous alkanes in the presence of an improved catalyst comprising zinc aluminate, tin dioxide, platinum and, optionally, calcium aluminate. It is a further object of this invention to alleviate coke formation in a process for dehydrogenating gaseous alkanes. Other objects and advantages will become apparent from the detailed description of the invention and the appended claims.

In accordance with this invention, in a process for dehydrogenating at least one alkane containing 2-8 carbon atoms per molecule to at least one alkene in the presence of steam and a catalyst composition comprising zinc aluminate, at least one tin oxide and platinum, wherein zinc aluminate has been prepared by a method comprising calcining alumina and zinc oxide, the improvement comprises employing at least one hydrated alumina in the method of preparing zinc aluminate. Preferably, calcium aluminate is also present in the catalyst composition.

DETAILED DESCRIPTION OF THE INVENTION

Figure 1:
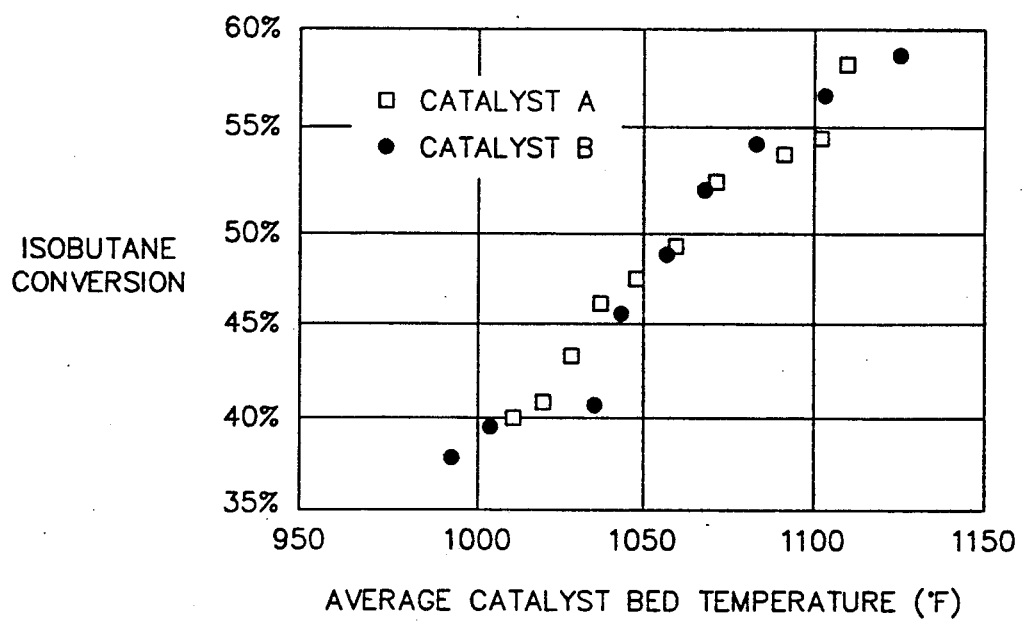
FIG. 1 compares the isobutane conversion in a dehydrogenation process attained with two $Pt/SnO_2/ZnAl_2O_4/CaAl_2O_4$ catalysts: Catalyst A which was prepared by a known method and Catalyst B which was prepared by a novel method employing a hydrated alumina.

The catalyst composition which is used in the dehydrogenation process of this invention is prepared by a method comprising mixing a hydrated alumina and zinc oxide, followed by heating under such conditions as to substantially convert hydrated alumina and zinc oxide to zinc aluminate spinel having the general formula of $ZnAl_2O_4$. Suitable hydrated aluminas which can be employed include crystalline alumina monohydrates, such as boehmite (presently preferred) and diaspore; crystalline alumina trihydrates such as gibbsite (hydrargillite), bayerite and nordstrandite; and substantially amorphous hydrated aluminas, such as pseudoboehmite. These hydrated aluminas are well known, and have been described in Kirk-Othmer Encyclopedia of Chemical Technology, Volume 2, Third Edition, pages 218-225. Preferred hydrated aluminas are boehmite, pseudoboehmite, bayerite, and mixtures of two or three of these materials. Boehmite is presently most preferred.

In the presently preferred method of preparation, the zinc aluminate is prepared by a method comprising mixing (preferably dry-blending in a suitable ball mill) appropriate amounts (preferably approximately equimolar amounts) of zinc oxide and hydrated alumina, drying the mixture (preferably at about 150°-250° C.), and then calcining (preferably by heating in air) the dried mixture at a sufficiently high temperature (preferably at about 750°-1200° C., more preferably about 750°-1000° C.) for a sufficient length of time (preferably about 1-10 hours) to form zinc aluminate. Preferably, at least one tin oxide (i.e., SnO and/or $SnO_2$; preferably $SnO_2$) and calcium aluminate ($CaAl_2O_4$, a binder) have also been added during the mixing, and are present during drying/calcining of the mixture.

A processing aid (such as graphite) can also be present during this mixing step. It is further preferred to add water or a dilute aqueous acid solution (such as a dilute acetic acid solution (generally containing about 0.5-5 volume-% $CH_3CO_2H$) during the mixing step, more preferably after hydrated alumina, zinc oxide and other components (such as $SnO_2$ and $CaAl_2O_4$) have been dry-blended. The time required for thorough dry-blending and subsequent mixing with water or an aqueous acid solution depends on the particular mixing equipment, the amounts of ingredients to be mixed and other operating parameters, and can easily be determined by those skilled in the art. The wet mixture can then be extruded through suitable dies, pelletized or granulated, under suitable conditions which can be easily determined by those skilled in the art.

The calcined zinc aluminate containing composition (preferably also containing $SnO_2$ and $CaAl_2O_4$) is used as a support material for the Pt promoter, and is impregnated with at least one dissolved platinum compound (such as $H_2PtCl_6$ in any suitable manner, followed by drying (preferably at about 80°-250° C.) and calcining (preferably at about 400°-600° C.); as has been described in the patent literature. Preferably, the calcined catalyst composition is washed with water to remove chloride ions, and is subsequently dried and calcined again (as described above). Subsequent heating of the catalyst composition in a reducing gas (such as $H_2$) can be carried out but, generally, is not necessary.

The components of the catalyst composition generally are present at the following levels: about 80-98 weight-% of zinc aluminate; about 0.05-5 weight-% of Pt; and about 0.1-5 weight-% of Sn (present as oxide, preferably $SnO_2$). It is understood that additional components which are beneficial for catalyzing the dehydrogenation of saturated hydrocarbons may also be present in small amounts, such as Re, Au, Ag, alkali metal, Ce, and the like. Suitable inorganic binder materials (preferably $CaAl_2O_4$, more preferably about 1-25 weight-% $CaAl_2O_4$, based on the weight of the finished catalyst composition) can also be present. Generally, the surface area of the finished catalyst composition is in the range of from about 5 to about 100 $m^2/g$ (determined by nitrogen adsorption in accordance with the BET method). The catalyst composition particles can have any suitable size and shape (such as cylindrical or spherical or granules or trilobal).

Any suitable paraffin containing 2-8 carbon atoms per molecule (normal alkane(s) or isoalkane(s) or mixtures thereof) can be used as feed in the dehydrogenation process of this invention. Preferred paraffins are ethane, propane, n-butane, isobutane, n-pentane, 2-methylbutane, and mixtures thereof. Particularly preferred are propane, n-butane and isobutane; most preferably isobutane.

The operating conditions of the dehydrogenation step of the invention are well known and have been described in numerous patents. Steam is present to alleviate coke deposition on the catalyst, to enhance feed conversion, and to retard catalyst deactivation. The reaction temperature in the dehydrogenation process is considerably higher than the normal boiling temperature (measured at 1 atm.) of the feed alkane. The reaction temperature in the dehydrogenation step generally is in the range of from about 500° to about 650° C., preferably about 560°-610° C. The molar ratio (essentially equal to volume ratio) of steam to the alkane(s) in the vaporized feed generally is in the range of from about 0.5:1 to about 30:1 (preferably from about 2:1 to about 10:1). The pressure in the dehydrogenation process generally is in the range of from about 0 to about 200 psig, and preferably is about 20-100 psig.

In the dehydrogenation process of this invention, generally steam and vaporized alkane, preferably premixed at the desired molar ratio, are preheated and passed through the dehydrogenation reactor (or a train of two or more reactors in series or in parallel) containing a fixed bed of the catalyst composition. The gas hourly space velocity of the vaporized alkane feed (excluding steam) in the dehydrogenation process generally is in the range of from about 100 to about 10,000 cc alkane per cc catalyst per hour, preferably from about 500 to about 2,000 cc/cc/hour. The flow rate of steam is determined by the desired volume (molar) ratio of steam to alkane feed (as disclosed above). Free oxygen is substantially absent during the dehydrogenation step of this invention since $O_2$ causes the formation of higher amounts of undesirable carbon oxides (CO and/or $CO_2$) during the process.

During the paraffin dehydrogenation process, the catalyst composition loses some of its catalytic activity, in part because of coke formation on the catalyst surface. When the catalytic activity has dropped below an effective level (generally after about 6-30 hours on stream), the flow of the alkane-containing feed is cut off, and a purge gas comprising steam and/or an inert gas (e.g., $N_2$, Ar, He) is passed through the hot catalyst bed (at a temperature of about 500°-650° C., for about 1-60 minutes), so as to substantially remove hydrocarbons from the reactor. Subsequently, the catalyst composition is regenerated, preferably by treating the catalyst composition for a suitable time with a free oxygen containing gas, preferably a stream of steam-diluted air, as is described in U.S. Pat. No. 4,613,715. Generally, the regeneration temperature is in the range of from about 450° to about 750° C. (preferably about 500°-700° C.), and the molar ratio (volume ratio) of steam to free oxygen is in the range of from about 40:1 to about 200:1. The flow rate of steam during catalyst regeneration is approximately the same as in the dehydrogenation step. The pressure during the regeneration cycle generally is about 0-200 psig, preferably about 20-100 psig. The duration of the regeneration step depends on the regeneration conditions and on the amount of coke deposits to be removed. Generally, the regeneration step is carried out for about 0.1 to about 5 hours, preferably about 0.2-1 hour. Thereafter, the reactor is purged again with a gas comprising steam and/or an inert gas (to sweep out $O_2$), the flow of the alkane feed is resumed, and the dehydrogenation is carried out with the regenerated catalyst composition (until the next catalyst regeneration phase is required).

The product of the dehydrogenation process comprises primarily monoolefins (alkenes). By-products include CO, $CO_2$ and diolefins. Some cycloalkanes, cycloalkadienes and aromatics can also be formed as by-products, especially when the feed paraffin contains 6-8 carbon atoms per molecule. When propane is used as feed, primarily propylene is formed; when n-butane is used, primarily butene-1 and butene-2 are formed; when isobutane is used as feed, primarily isobutene is formed; when n-pentane is used, primarily pentene-1 and pentene-2 are formed; and when 2-methylbutane is used, primarily 2-methylbutene-1 and 2-methylbutene-2 are formed. The formed monoolefinic hydrocarbons can be recovered after having been separated from other components of the reaction product mixture of the dehydrogenation process by any suitable means, e.g., by fractional distillation (preferably at a low temperature and a high pressure) or by well known absorption/desorption processes or by membrane separation techniques. Unreacted hydrocarbon feed, after it has been substantially separated from other reaction product components, can be recycled to the dehydrogenation reactor which contains the catalyst composition.

The following examples are presented to further illustrate the invention and are not to be construed as unduly limiting the scope of the claimed invention.

EXAMPLE I

This example illustrates the preparation of two dehydrogenation catalysts which comprise platinum, tin dioxide, zinc aluminate and calcium aluminate. In the preparation of both catalysts, the zinc aluminate support material was prepared by calcining alumina and zinc oxide; however, different aluminas were employed.

Catalyst A (Control) was prepared as follows: 1.3 lb. of tin dioxide (Harshaw Spec 101; provided by Harshaw Chemical Co., Cleveland, Ohio), 10.0 lb. of calcium aluminate (Secar 71 Cement; provided by LaFarge Calcium Aluminates, Chesapeake, Va.), 39.8 lb. of zinc oxide (St. Joe's #922; provided by St. Joe Resources, Monaca, Pa.), and 52.2 lb. of gamma alumina (flame-hydrolyzed Degussa "C", having a loss on ignition of about 5.4 wt-%; provided by Degussa, Ridgefield Park, N.J.) were dry-blended for 4–5 minutes. Then 55 lb. of deionized water was added during a period of time of 5 minutes. Finally 3.75 lb. of high purity graphite (a processing aid) was added. The resulting paste was mixed for 2–3 minutes, and then dried at about 350° F. The dried granular material was screened through a 14 mesh screen, the fraction which passed through the screen was tabletted in a tabletting machine, equipped with dies to make $\frac{1}{8}'' \times \frac{1}{8}''$ tablets, at a pressure of about 140 lb.

Thereafter, the tablets were treated in a hot water autoclave in accordance with the following schedule: 2 hours at 300° F., 2 hours at 650° F. and 2 hours at 950° F. Then the pellets were calcined in air for 4 hours at 1550°–1600° F. X-ray diffraction analytical results indicated that 95 weight-% of the material was $ZnAl_2O_4$.

An aqueous solution of $H_2PtCl_6$, having a Pt content sufficient to deposit 0.6 weight percent Pt on the support, was sprayed onto the calcined $ZnAl_2O_4$-containing pellets in a cement mixer type coating apparatus. The thus-impregnated wet catalyst material was dried at 350° F. for 4 hours and then calcined in air at 900° F. for 2 hours. The calcined catalyst particles contained 0.57 weight-% Pt and 0.84 weight-% Cl. In order to substantially remove chloride ions, the calcined catalyst was soaked for 1 hour in a caustic solution of 4.25 lb NaOH in 38–40 gallons of deionized water at 80° F. Then the caustic solution was drained, and the catalyst particles were washed about 17 times with deionized water, so as to lower the chloride content in the catalyst to less than 100 ppm Cl, followed by drying in air at 350° F.

Catalyst B (Invention) was prepared as follows: 744 g of a boehmite alumina (provided by Vista Chemical Company, Houston, Tex., under the product designation "Dispal"), 591 g of zinc oxide (described above), 19.5 g of tin dioxide (described above) and 131.4 g of calcium aluminate (described above) were dry-blended for about 10 minutes in a mix-muller. To the dry mixture was slowly added 825 mL of an aqueous 1 volume-% acetic acid solution over a period of 15 minutes while the mixing was continued. Thereafter, 28.8 g of high purity graphite was added, with mixing, over a period of 15 minutes. The resulting paste was dried at 200° C. overnight in a Blue M circulating air oven. The dried material was ground, sieved and pelletized (substantially as described for Catalyst A) and calcined in air at 1550° F. for 5 hours. 1056 grams of the calcined $\frac{1}{8}'' \times \frac{1}{8}''$ pellets were then impregnated with an aqueous solution of 16.7 g $H_2PtCl_6$ in 281 g distilled water, followed by drying, calcining, frequent washing with deionized water and drying, substantially as described for Catalyst A.

EXAMPLE II

This example illustrates the dehydrogenation of isobutane in the presence of the two $Pt/SnO_2/ZnAl_2O_4/CaAl_2O_4$ catalysts described in Example I (Catalyst A having been prepared from gamma-alumina and Catalyst B having been prepared from boehmite). Isobutane and steam were introduced into a pilot plant reactor having a length of about 2 feet and a diameter of about 2 inches. The reactor was filled with a layer (about 14 inches high) of about 770 cc of either Catalyst A or Catalyst B.

Liquid isobutane was vaporized and mixed with superheated steam at a weight ratio of steam to isobutane of 1.23:1 (equivalent to a molar ratio of steam to isobutane of 3.95:1). The isobutane/steam mixture was heated to 1050° F. and introduced into the reactor at a rate of 1728 g/hour of isobutane and 2125 g/hour of steam. The temperature of the catalyst bed was varied from about 950° F. to about 1120° F., and the average reaction pressure was about 50 psig. The exiting product of gas was analyzed for isobutane and isobutene by means of a gas chromatograph.

Generally, the mixture of isobutane and steam was passed through the reactor for about 7 hours. Then the isobutane flow was discontinued, and the reactor was purged with steam (about 2100 g/minute) for 5–10 minutes. Thereafter, air was introduced into the reactor at a rate of about 10 standard cubic feet per hour (SCFH) for about 25 minutes, and then at a rate of about 20 SCFH for about 25 minutes, while the steam flow rate remained about 2100 g/hour, so as to burn off coke deposits. The amount of coke deposits on the catalyst was determined by means of a gas chromatograph from the amount of $CO_2$ formed during the regeneration cycle. Subsequently, the flow of air was discontinued, and a purge stream of steam was passed through the reactor for 5 minutes, before isobutane was introduced again for another dehydrogenation cycle.

Figure 2:
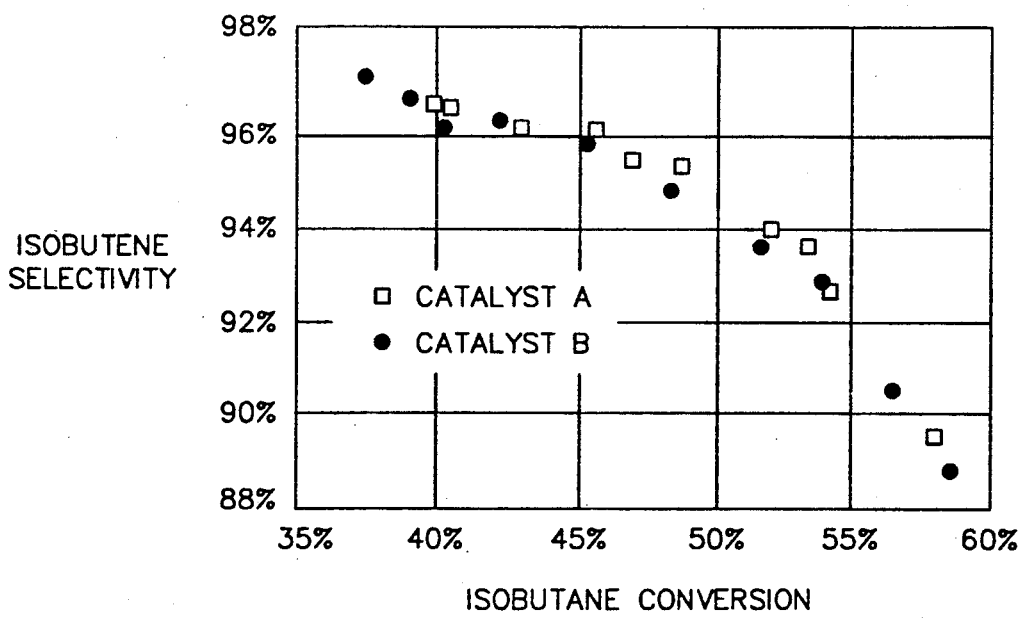
FIG. 2 depicts the correlation between selectivity to isobutene and isobutane conversion attained with two dehydrogenation catalysts: Catalyst A which was prepared by a known method and Catalyst B which was prepared by a novel method employing a hydrated alumina.
Figure 3:
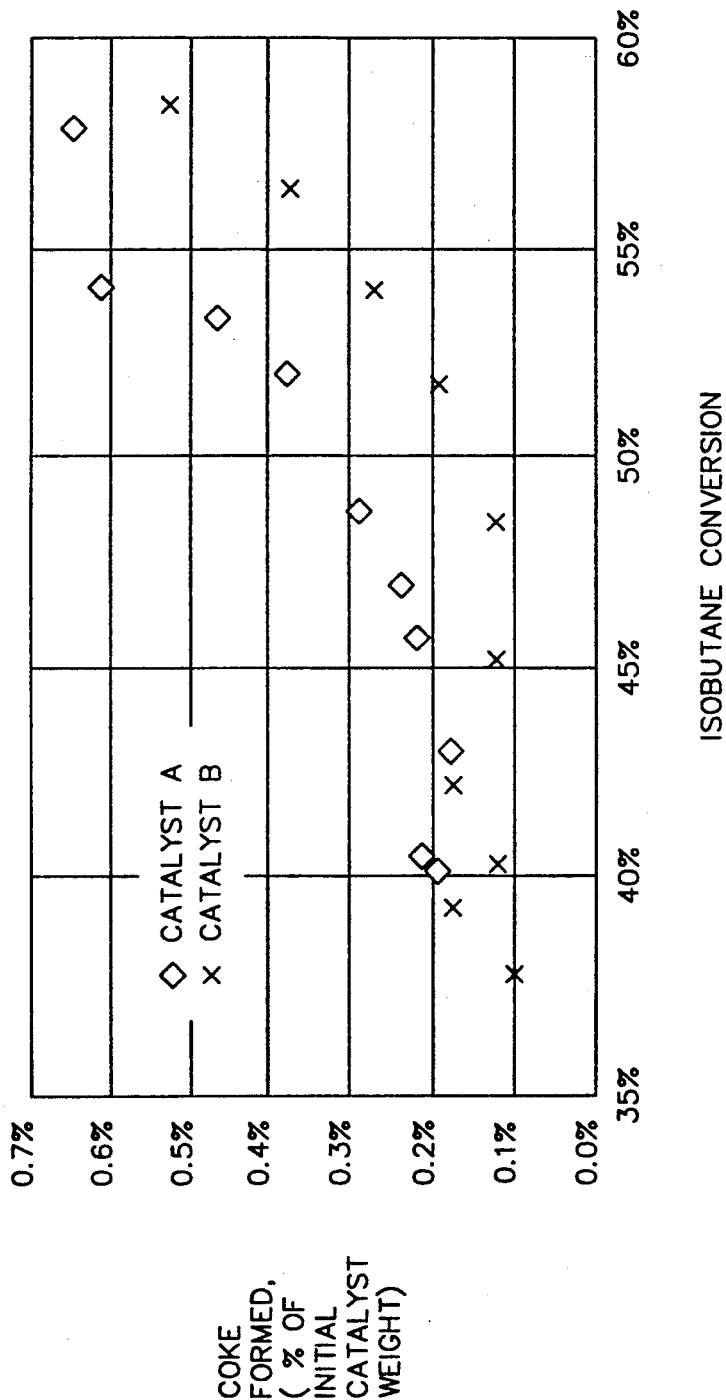
FIG. 3 depicts the correlation between coke formation and isobutane conversion attained with two dehydrogenation catalysts: Catalyst A which was prepared by a known method and Catalyst B which was prepared by a novel method employing a hydrated alumina. Use of Catalyst B resulted in less coking.

Test results for Catalysts A and B are depicted in the Figures. FIG. 1 and FIG. 2 show that isobutane conversion and %-selectivity to isobutene (i.e., the mole-percentage of converted isobutane which had been dehydrogenated to isobutene) were approximately the same for Catalyst A and Catalyst B. However, as shown in FIG. 3, the amount of coke deposits, at equal isobutane conversion, was noticeably lower for Catalyst B (prepared from hydrated boehmite alumina). This result indicates that Catalyst B would deactivate at a lower rate, permitting longer dehydrogenation cycles (before the regeneration of the catalyst).

Reasonable variations, modifications and adaptations for various usages and conditions can be made within the scope of the disclosure and the appended claims, without departing from the scope of this invention.

That which is claimed is:

1. In a process for dehydrogenating at least one alkane containing 2–8 carbon atoms per molecule to at least one alkene in the presence of steam and a catalyst composition consisting essentially of about 80–98 weight-% zinc aluminate, at least one tin oxide being present at a level equivalent to about 0.1–5 weight-% tin, about 0.05–5 weight-% platinum, and calcium aluminate, wherein said zinc aluminate has been prepared by a preparation method comprising calcining alumina and zinc oxide, the improvement which comprises employing hydrated alumina in said preparation method.

2. A process in accordance with claim 1, wherein said hydrated alumina is selected from the group consisting of boehmite, pseudoboehmite and bayerite.

3. A process in accordance with claim 1, wherein said hydrated alumina is boehmite.

4. A process in accordance with claim 1, wherein said calcining of hydrated alumina and zinc oxide is carried out at a temperature of about 750°–1200° C.

5. A process in accordance with claim 1, wherein said at least one tin oxide is tin dioxide.

6. A process in accordance with claim 1, wherein said preparation method comprises mixing hydrated alumina and zinc oxide and thereafter calcining the thus-obtained mixture at a temperature of about 750° C. to about 1200° C., under such conditions as to form zinc aluminate.

7. A process in accordance with claim 6, wherein tin dioxide and calcium aluminate are additionally present in said thus-obtained mixture which is thereafter calcined.

8. A process in accordance with claim 7, wherein the calcined mixture is impregnated with at least one dissolved platinum compound, followed by drying, calcining, washing with water, drying and calcining.

9. A process in accordance with claim 1, wherein said dehydrogenating is carried out at a temperature in the range of from about 500° C. to about 650° C. and a molar ratio of steam to said at least one alkane in the range of from 0.5:1 to about 30:1.

10. A process in accordance with claim 1, wherein said at least one alkane is selected from the group consisting of propane, n-butane, isobutane, n-pentane and 2-methylbutane.

11. A process in accordance with claim 1, wherein said at least one alkane is isobutane.

12. A process in accordance with claim 1, wherein said at least one alkene formed in said process is selected from the group consisting of propylene, butene-1, butene-2, isobutene, pentene-1, pentene-2, 2-methylbutene-1 and 2-methylbutene-2.

13. A process in accordance with claim 1, further comprising the additional step of interrupting the flow of said at least one alkane, regenerating said catalyst composition by heating it with a free oxygen containing gas at a temperature of about 450°–750° C. for about 0.1–5 hours, and reusing the thus-regenerated catalyst composition for dehydrogenating said at least one alkane.

* * * * *